(12) United States Patent
Otsubo et al.

(10) Patent No.: US 7,189,301 B2
(45) Date of Patent: *Mar. 13, 2007

(54) PROCESS FOR ATTACHING INDICATOR ELEMENT TO DISPOSABLE GARMENT

(75) Inventors: Toshifumi Otsubo, Kagawa-ken (JP); Hiroki Yamamoto, Kagawa-ken (JP)

(73) Assignee: Uni-Charm Co., Ltd., Ehime-ken (JP)

( * ) Notice: Subject to any disclaimer, the term of this patent is extended or adjusted under 35 U.S.C. 154(b) by 108 days.

This patent is subject to a terminal disclaimer.

(21) Appl. No.: 11/015,867

(22) Filed: Dec. 20, 2004

(65) Prior Publication Data

US 2005/0103436 A1 May 19, 2005

Related U.S. Application Data

(63) Continuation of application No. PCT/JP2003/09261, filed on Jul. 22, 2003.

(30) Foreign Application Priority Data

Aug. 15, 2002 (JP) .............................. 2002-236947

(51) Int. Cl.
   *B32B 37/00* (2006.01)
(52) U.S. Cl. ...................................... 156/269; 156/302
(58) Field of Classification Search ................ 156/160, 156/163, 164, 229, 250, 269, 290, 297, 302, 156/308.2, 308.4
   See application file for complete search history.

(56) References Cited

U.S. PATENT DOCUMENTS 6,558,499 B1 * 5/2003 Pargass et al. .............. 156/250

6,788,803 B2 * 9/2004 Calvert ........................ 382/111
2005/0067083 A1 * 3/2005 Vergona ....................... 156/64
2005/0092427 A1 * 5/2005 Vergona ...................... 156/250

FOREIGN PATENT DOCUMENTS

| EP | 1 078 620 A2 | 2/2001 |
|---|---|---|
| JP | 2-234760 | 9/1990 |
| JP | 04-161152 | 6/1992 |
| JP | 10-118116 | 5/1998 |
| JP | 2001-054536 | 2/2001 |

* cited by examiner

*Primary Examiner*—James Sells
(74) *Attorney, Agent, or Firm*—Lowe Hauptman & Berner LLP

(57) ABSTRACT

In a process for attaching indicator elements onto a disposable garment, liquid-absorbent cores and indication sheets each having indicator elements are fed onto inner and outer surfaces of an outer layer web. A rear half of the front sheet of adjacent indication sheets placed upon a front end of the core and a front half of the rear sheet of the adjacent indication sheets placed upon a rear end of the core. The indication sheet is joined to the outer layer web, the core is joined to the inner and outer layer webs, and the webs are joined together. The indication sheet is cut together with the inner and outer layer webs between adjacent cores to obtain inner panels arranged in the machine direction. The inner panels are turned to the cross direction, and arranged on the inner surface of an outer web, and the outer layer web is joined to the outer web.

11 Claims, 10 Drawing Sheets

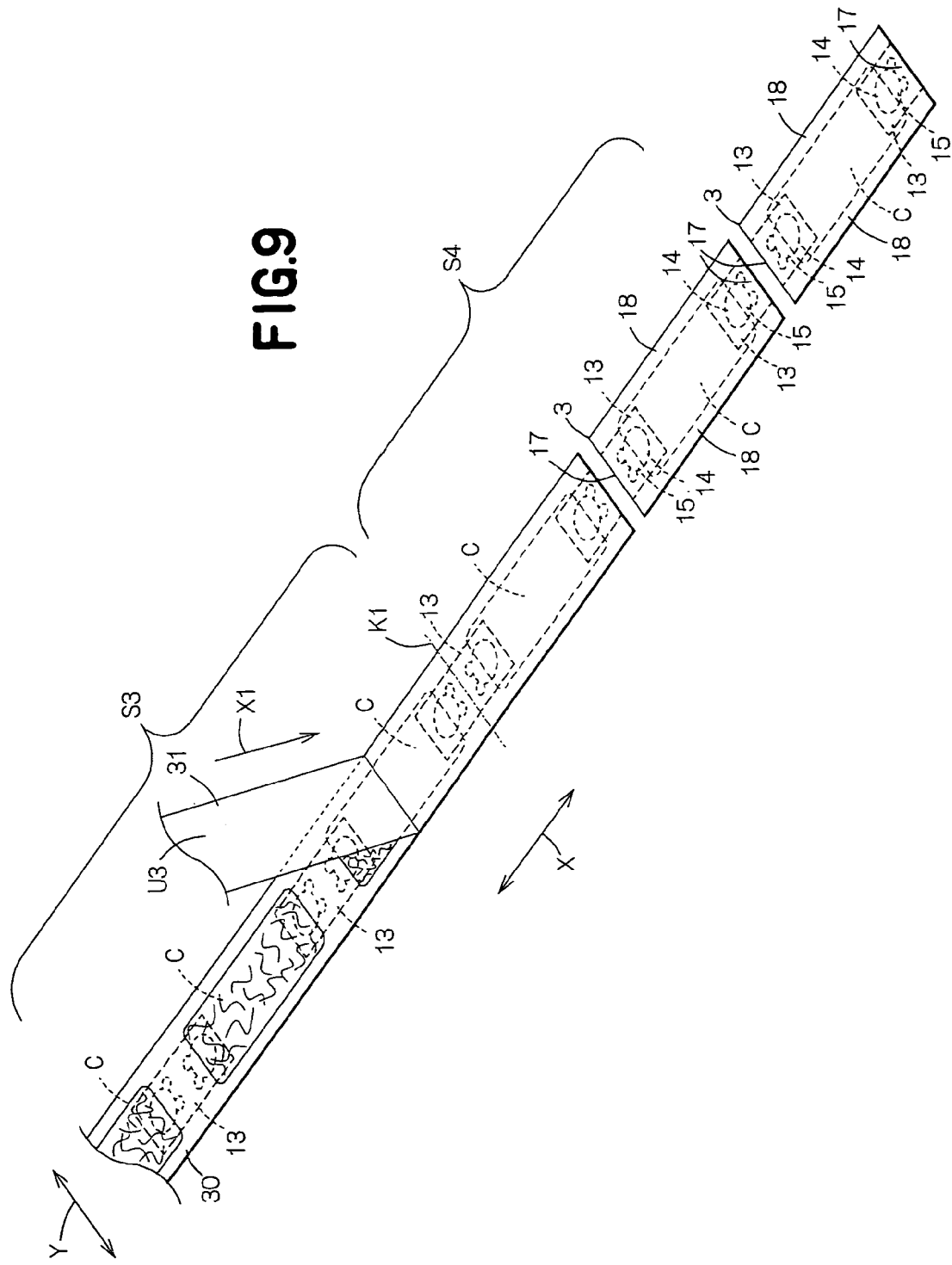

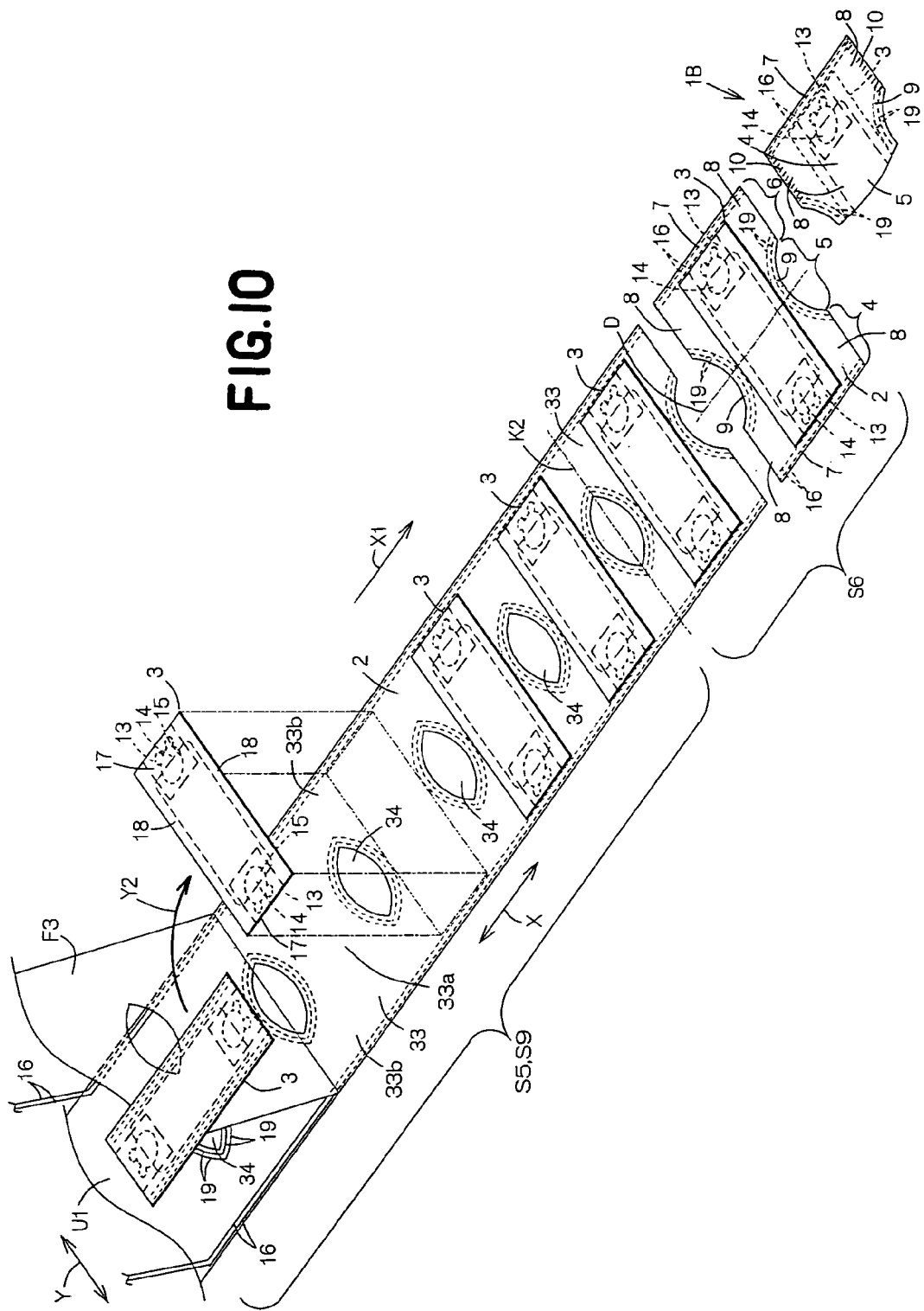

PROCESS FOR ATTACHING INDICATOR ELEMENT TO DISPOSABLE GARMENT

This application is a continuation of International Application No. PCT/JP2003/09261 filed Jul. 22, 2003, which claims priority to Japanese Application No. 2002-236947 filed Aug. 15, 2002, all of which are hereby incorporated by reference herein in their entirety.

BACKGROUND OF THE INVENTION

This invention relates to a process for attaching, in front and rear waist regions of a disposable garment such as a diaper comprising an outer sheet and a liquid-absorbent inner panel attached to the outer sheet, indicator elements which are visually recognizable from the exterior of the garment.

Japanese Patent Application Publication No. 2001-54536A discloses a pull-on disposable article including a patterned sheet and a process for making the same. This diaper comprises a liquid-impervious backsheet lying on the side facing away from a wearer's body (outer layer web), a liquid-pervious topsheet (inner layer web) lying on the side facing the wearer's body, and a liquid-absorbent core interposed between these sheets. This article has a front waist region, a rear waist region, a crotch region extending between these waist regions, a waist-opening and a pair of leg-openings. The patterned sheet adapted to be visually recognizable from the exterior of the article is attached to an inner surface of the outer sheet.

The process for making this diaper comprises a step of attaching the patterned sheet in which the patterned sheet having an area smaller than the outer sheet is attached to the inner surface of the outer sheet at a predetermined location, a step of securing the core in which the core is secured to the inner surface of the outer sheet and a step of joining the sheets in which the inner sheet is placed upon and joined with the upper surface of the core. In the step of attaching the patterned sheet, a plurality of the patterned sheets are successively fed onto the inner surface of the outer sheet so as to be spaced one from another by a predetermined dimension in a longitudinal direction of the outer sheet and then these patterned sheets are attached to the outer sheet by means of a hot melt adhesive.

According to the process for making the diaper as disclosed in the above-cited Publication, a plurality of the patterned sheets must be individually fed onto and attached to the inner surface of the outer sheet with each pair of the patterned sheets being spaced apart from each other by a predetermined dimension in a transverse dimension. Feeding and attaching of these patterned sheets inevitably doubles time and labor and require the additional device as well as steps associated with such feeding as well as such attaching. Consequently, it is impossible to manufacture the diapers at a low cost.

It is an object of this invention to provide a process for attaching indicator elements all at once on surfaces front and rear regions of the diaper.

According to the present invention, there is provided a process for attaching, in front and rear regions of a disposable garment which comprises an outer sheet and a liquid-absorbent inner panel attached to the outer sheet, indicator elements which are visually recognizable from an exterior of the article.

The improvement according to the present invention is characterized by that the process comprising the steps of: feeding a plurality of liquid-absorbent cores each having front and rear end zones and an intermediate zone and running in a machine direction onto an inner surface of one of a continuous first outer layer web and a continuous inner layer web running in a machine direction and destined to be the outer sheet while feeding a plurality of indication sheets each extending in the machine direction and having the indicator elements in front and rear halves thereof, respectively, at regular intervals in the machine direction onto an outer surface of the first outer layer web; placing the intermediate zone of the core between each pair of the indication sheets adjacent to each other in the machine direction, so that a rear half of a front one of the indication sheets adjacent to each other in the machine direction is placed upon the front end zone of the core, and a front half of a rear one of the indication sheets adjacent to each other in the machine direction is placed upon the rear end zone of the core; joining the indication sheet to the first outer layer web, joining the core to at least one of the inner layer web and the outer layer web and joining inner surfaces of the inner layer web and the outer layer web overlaid; forming a panel by cutting the indication sheets together with the inner and outer layer webs in a cross direction between a pair of the cores adjacent to each other in the machine direction so that the indication sheet is divided into the front and rear halves to obtain a plurality of the inner panels arranged in the machine direction; and placing the inner panels at regular intervals on an inner surface of a continuous outer web running in the machine direction after the inner panels are turned round in the transverse direction approximately by 90° and joining the outer surface of the first outer layer web to an inner surface of the outer web.

The present invention includes the following embodiments.

(1) The process further includes the steps of cutting the outer web in a transversely middle zone to form a plurality of openings arranged at regular intervals in the machine direction then, placing between each pair of the openings adjacent to each other of the outer web after turning round the inner panels approximately by 90° to a cross direction and cutting the outer web in the cross direction between each pair of the inner panels adjacent to each other to form a plurality of the garment arranged in the machine direction.

(2) The process further includes the stop of turning round the inner panels approximately by 90° to a cross direction while placing the inner panels on the inner surface of the outer web at regular intervals in the machine direction and then, cutting a transversely middle zone of the outer web extending between each pair of the inner panels adjacent to each other to form a plurality of openings arranged at regular intervals in the machine direction; and cutting the outer web in the cross direction between each pair of the inner panels adjacent to each other to form a plurality of the garment arranged in the machine direction.

(3) The process further includes the steps of placing an inner surface of a continuous second outer layer web running in the machine direction upon the outer surface of the first outer layer web, joining the first outer layer web to the second outer layer web; cutting the indication sheet together with the first and second outer layer webs and the inner layer web in the cross direction between each pair of the cores adjacent to each other in the machine direction; and joining the outer surface of the second outer layer web to the inner surface of the outer web.

(4) The process further includes the step of attaching first stretchable elastic members lying on both sides of the core and extending in the machine direction in a stretched state to one of an inner surface of the first outer layer web and an inner surface of the inner layer web.

(5) The process includes the step of attaching the first stretchable elastic members lying on both sides of the core and extending in the machine direction in a stretched state to one of the outer surface of the first outer layer web and the inner surface of the second outer layer web.

(6) The process further includes the step of attaching second stretchable elastic members lying on both sides of the outer web and extending in the machine direction in a stretched state to the outer web.

(7) The first and second outer layer webs are formed by one of a moisture-permeable hydrophobic fibrous nonwoven fabric and a moisture-permeable liquid-impervious plastic film and the inner layer web is formed by a hydrophilic fibrous nonwoven fabric.

(8) The outer layer web is formed by one of a moisture-permeable hydrophobic fibrous nonwoven fabric, a composite nonwoven fabric consisting of moisture-permeable but hydrophobic fibrous nonwoven fabric layers laminated one with another and a composite sheet consisting of a moisture-permeable but hydrophobic fibrous nonwoven fabric and a moisture-permeable but liquid-impervious plastic film laminated with each other.

(9) The indication sheet is formed by one of a moisture-permeable but hydrophobic fibrous nonwoven fabric and a moisture-permeable but liquid-impervious plastic film.

(10) The indicator elements comprise a pair of illustrations printed on the front and rear halves of the indication sheet and adjacent to each other in the machine direction.

BRIEF DESCRIPTION OF THE DRAWINGS

FIG. 9 is a perspective view schematically illustrating steps subsequent to the steps in the process illustrated in FIG. 8; and FIG. 10 is a perspective view schematically illustrating steps subsequent to the steps in the process illustrated in FIG. 9.

DETAILED DESCRIPTION OF THE PREFERRED EMBODIMENTS

Details of the process according to this invention for attaching the indicator element will be more fully understood from the description given hereunder with reference to the accompanying drawings.

Figure 1:
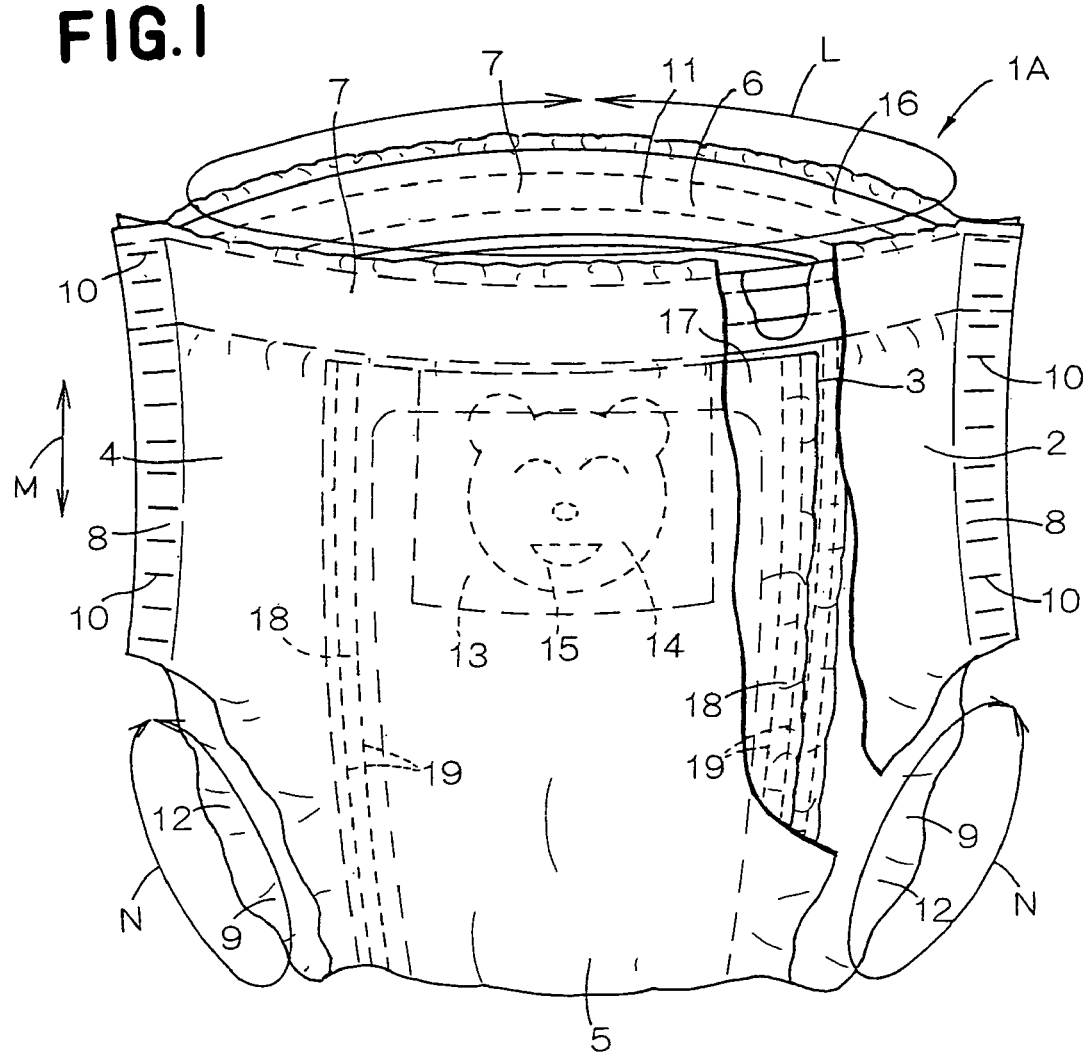
FIG. 1 is a partially cutaway perspective view showing a wearing article according to the invention.
Figure 2:
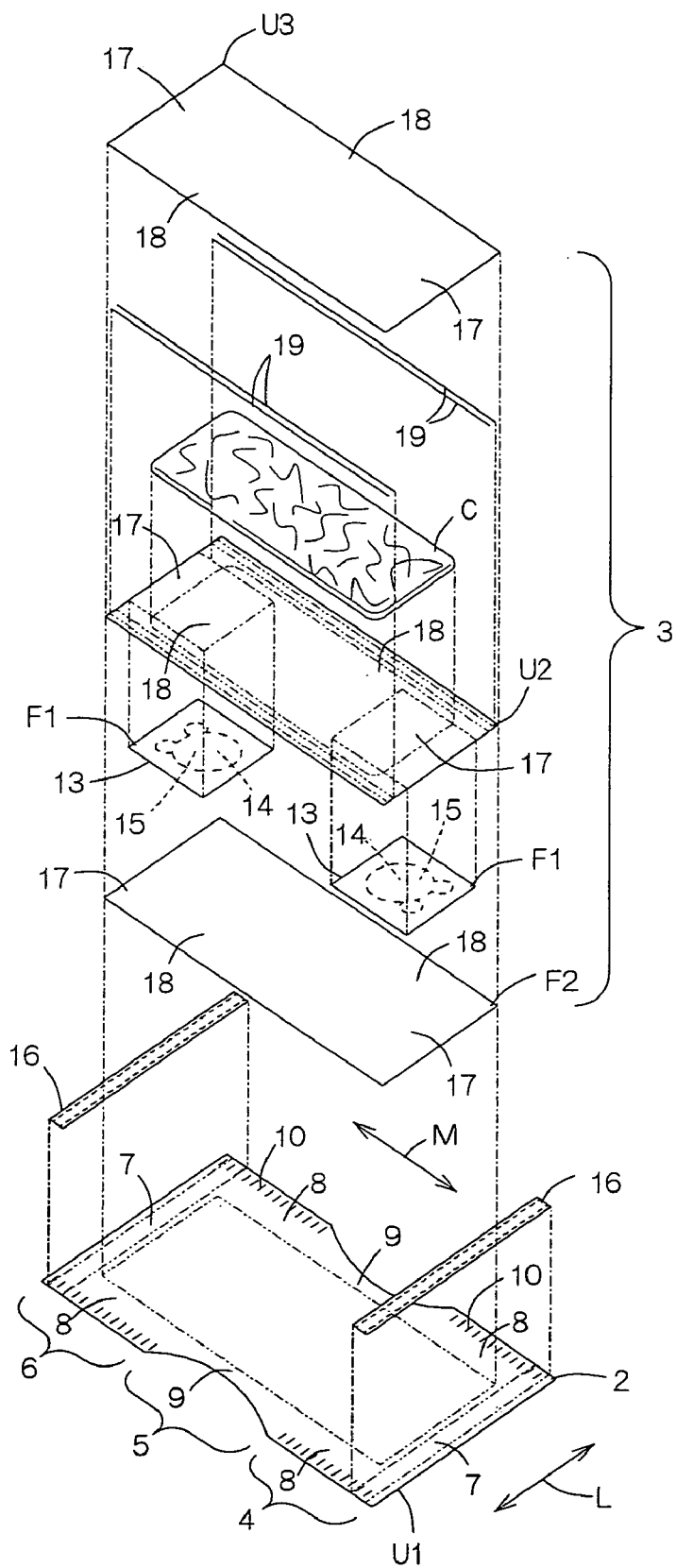
FIG. 2 is an exploded perspective view showing the article shown in FIG. 1.

FIG. 1 is a partially cut away perspective view showing a wearing article 1A made by a process for attaching the indicator element as will be described later and FIG. 2 is an exploded perspective view showing the article 1A of FIG. 1. In FIGS. 1 and 2, a waist-surrounding direction is indicated by an arrow L, a longitudinal direction is indicated by an arrow M and a leg-surrounding direction is indicated by an arrow N (in FIG. 1 alone). Expression "inner surfaces" of a fibrous nonwoven fabric layer U1 forming an outer sheet 2, fibrous nonwoven fabric layers U2, U3 forming an inner panel 3, a plastic film F2 and an indication sheet 13 refers to surfaces thereof facing a liquid-absorbent core C and expression "outer surfaces" thereof refers to surfaces facing away from the core C.

The article 1A is of pants-type and disposable after used. The article 1A comprises a substantially liquid-impervious outer sheet 2 and a liquid-absorbent inner panel 3 attached to the inner side of the outer sheet 2. The article 1A is composed of front and rear waist regions 4, 6 and a crotch region 5 extending between these waist regions 4, 6.

The article 1A has a waist-surrounding upper end zone 7 extending in the front and rear waist regions 4, 6 in the waist-surrounding direction, transversely opposite waist's lateral zones 8 extending in the front and rear waist regions 4, 6 in the longitudinal direction and transversely opposite legs' lateral zones 9 extending in the crotch region 5 in the leg-surrounding direction. The legs' lateral zones 9 describe circular arcs which are convex inwardly of the article 1A as viewed in the waist-surrounding direction. The article 1A has a generally hourglass-like planar shape when the article 1A is developed. In the article 1A, the waist's lateral zones 8 are overlaid and joined together by means of plural heat-sealing lines 10 arranged intermittently in the longitudinal direction. The article 1A has a waist-hole 11 and a pair of leg-holes 12 below the waist-hole 11.

The front and rear waist regions 4, 6 are provided in respective transversely middle zones thereof with an indication sheet 13 having indicator elements 14 adapted to be visually recognized from an exterior of the article 1A. Each of the indicator elements 14 comprises an illustration of a bear's face printed on the indication sheet 13. The indicator element 14 is not limited to such an illustration but may be in the form of pattern, letters or figures.

Alternatively, the front waist region 4 is provided in its transversely middle zone with the indication sheet 13 printed with an illustration while the rear waist region 6 is provided in its transversely middle zone with the indication sheet 13 printed with letters. It is also possible to provide the front waist region 4 in its transversely middle zone with the indication sheet 13 printed with an illustration of a bear's face and to provide the rear waist region 6 in its transversely middle zone with the indication sheet 13 printed with an illustration of a horse' face.

The outer sheet 2 is formed by the moisture-permeable but hydrophobic fibrous nonwoven fabric U1. The indication sheet 13 is formed by a moisture-permeable but liquid-impervious plastic film F1. Alternatively, the indication sheet 13 may be formed by a moisture-permeable but hydrophobic fibrous nonwoven fabric.

The waist-surrounding upper end zone 7 is provided with a band-like waist elastic member 16 (second stretchable elastic member) extending in the waist-surrounding direction attached thereto so as to be contractible. The elastic member 16 comprises band-like non-woven fabric layers and a plurality of stretchable elastic members which are wrapped up in and secured to the non-woven fabric layer in a stretched state and is attached to the inner surface of the outer sheet 2.

The panel 3 has a generally rectangular shape and extends over the crotch region 5 into the front and rear waist regions 4, 6. The panel 3 is formed by the moisture-permeable but hydrophobic fibrous nonwoven fabric layer U2 (first outer layer web) lying on a side facing away from a wearer's body, the moisture-permeable but liquid-impervious plastic film F2 (second outer layer web), the moisture-permeable and hydrophilic fibrous nonwoven fabric layer U3 (inner layer web) lying on a side facing the wearer's body and a liquid-absorbent core C interposed between these nonwoven fabric layers U2, U3 (See FIG. 2). The panel 3 has longitudinally opposite end zones 17 extending in the waist-surrounding direction and transversely opposite side edge zones 18 extending in the longitudinal direction. Portions of the nonwoven fabric layers U2, U3 extending outward beyond a periphery of the core C have respective inner surfaces overlaid and joined together.

A plurality of leg elastic members 19 (first stretchable elastic members) are attached to the side edge zones 18 of the panel 3 so that these elastic members 19 may extend in the leg-surrounding direction and be contractible in this direction. The leg elastic members 19 are interposed between the nonwoven fabric layers U2, U3 and secured to inner surfaces of these nonwoven fabric layers U2, U3. Alternatively, the leg elastic members 19 may be interposed between the nonwoven fabric layer U2 and the film F2 and secured to the inner and outer surfaces of these layer U2 and film F2. The panel 3 is attached to the inner surface of the outer sheet 2 by securing an outer surface of the film F2 to the inner surface of the outer sheet 2 by means of a hot melt adhesive (not shown).

The nonwoven fabric layer U2 and the film F2 respectively have their areas slightly larger than that of a lower surface of the core C and cover an entire lower surface of the core C. The nonwoven fabric layer U3 has its area slightly larger than that of an upper surface of the core C and covers the entire upper surface of the core C. The nonwoven fabric layer U2 has its inner surface secured to the lower surface of the core C by means of a hot melt adhesive (not shown). The nonwoven fabric U2 and the film F2 respectively have their inner and outer surfaces joined together by means of a hot melt adhesive (not shown). The nonwoven fabric layer U3 has its inner surface secured to the upper surface of the core C by means of a hot melt adhesive (not shown). The indication sheet 13 is interposed between the nonwoven fabric layer U2 and the film F2 and has its inner surface joined to an outer surface of the nonwoven fabric layer U2 by means of a hot melt adhesive (not shown). The film F2 and the indication sheet 13 are left free from each other.

The core C comprises a mixture of fluff pulp and super-absorbent polymer particles or a mixture of fluff pulp, super-absorbent polymer particles and thermoplastic synthetic resin fibers, in any case, compressed to a desired thickness. Preferably, the core C is entirely wrapped with a liquid-pervious sheet such as a tissue paper or a hydrophilic fibrous nonwoven fabric layer in order to prevent the core C from getting out of its initial shape and/or to prevent the polymer particles from falling off from the core C.

The adhesive is applied on the entire inner and outer surfaces of the nonwoven fabric layer U2, the entire inner surface of the nonwoven fabric layer U3 and the entire outer surface of the film F2. It is also possible to coat the entire inner surface of the film F2 with an adhesive. In this case, the outer surface of the indication sheet 13 is joined to the inner surface of the film F2.

The pattern in which the adhesive is applied on the nonwoven fabric layers U2, U3 and the film F2 is preferably selected from the group consisting of spiral-, zigzag-, dot- and stripe-patterns. Application of the adhesive in such patterns defines the adhesive-coated zones and the adhesive-free zones in the nonwoven fabric layers U2, U3 and the film F2.

Figure 3:
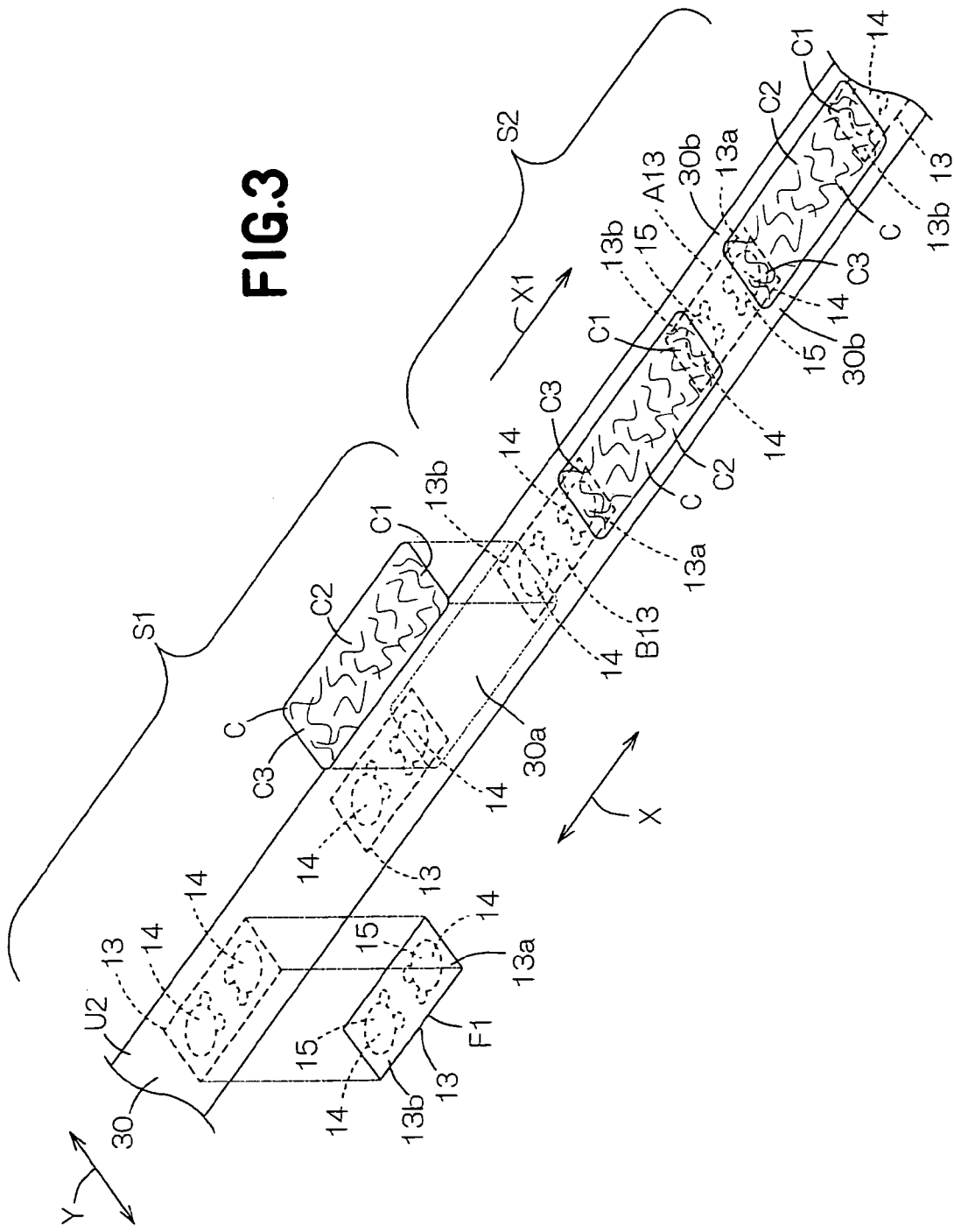
FIG. 3 is a perspective view schematically illustrating an embodiment of the process for attaching an indicator element.
Figure 4:
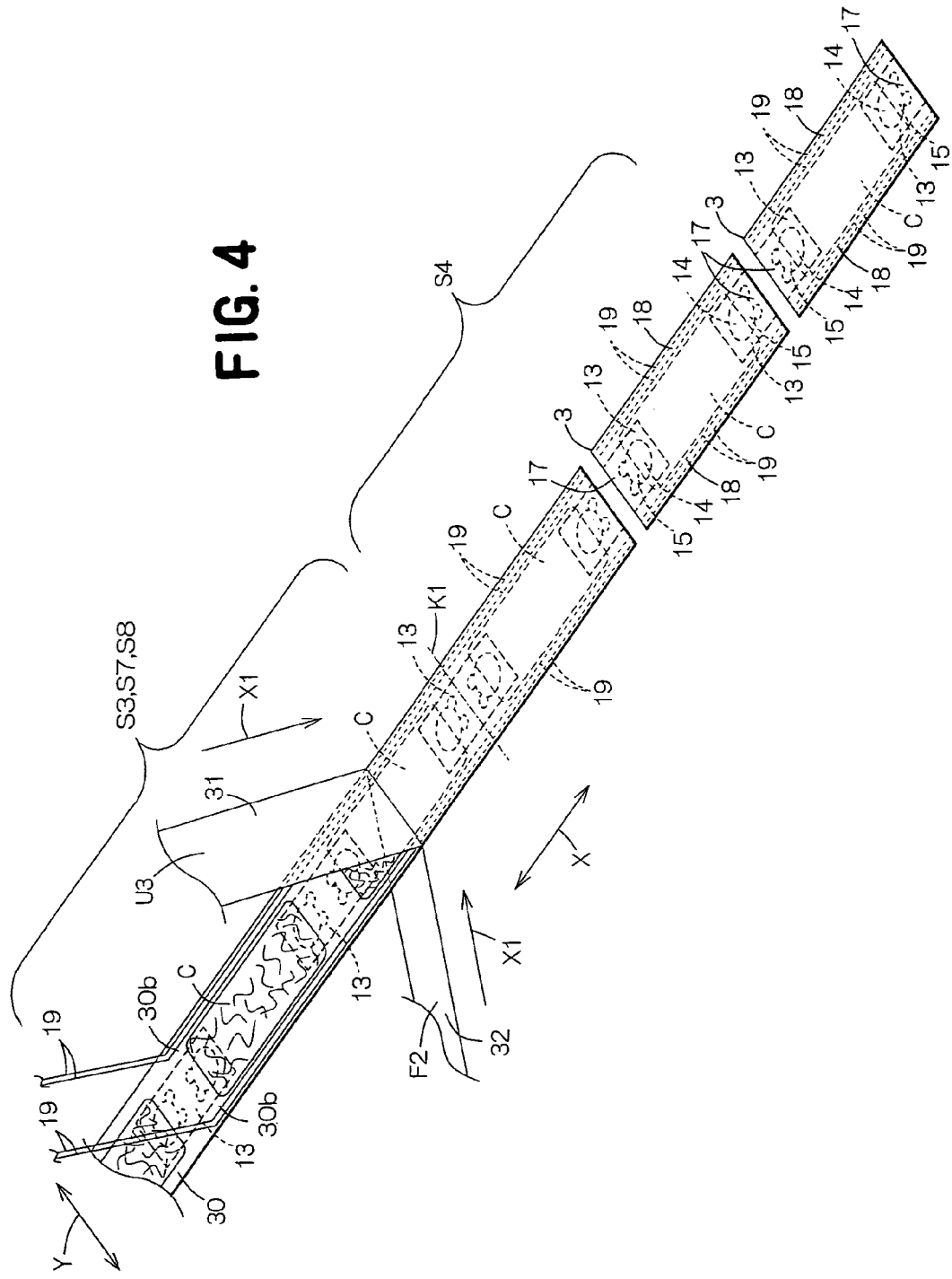
FIG. 4 is a perspective view schematically illustrating steps subsequent to the steps in the process illustrated in FIG. 3.
Figure 5:
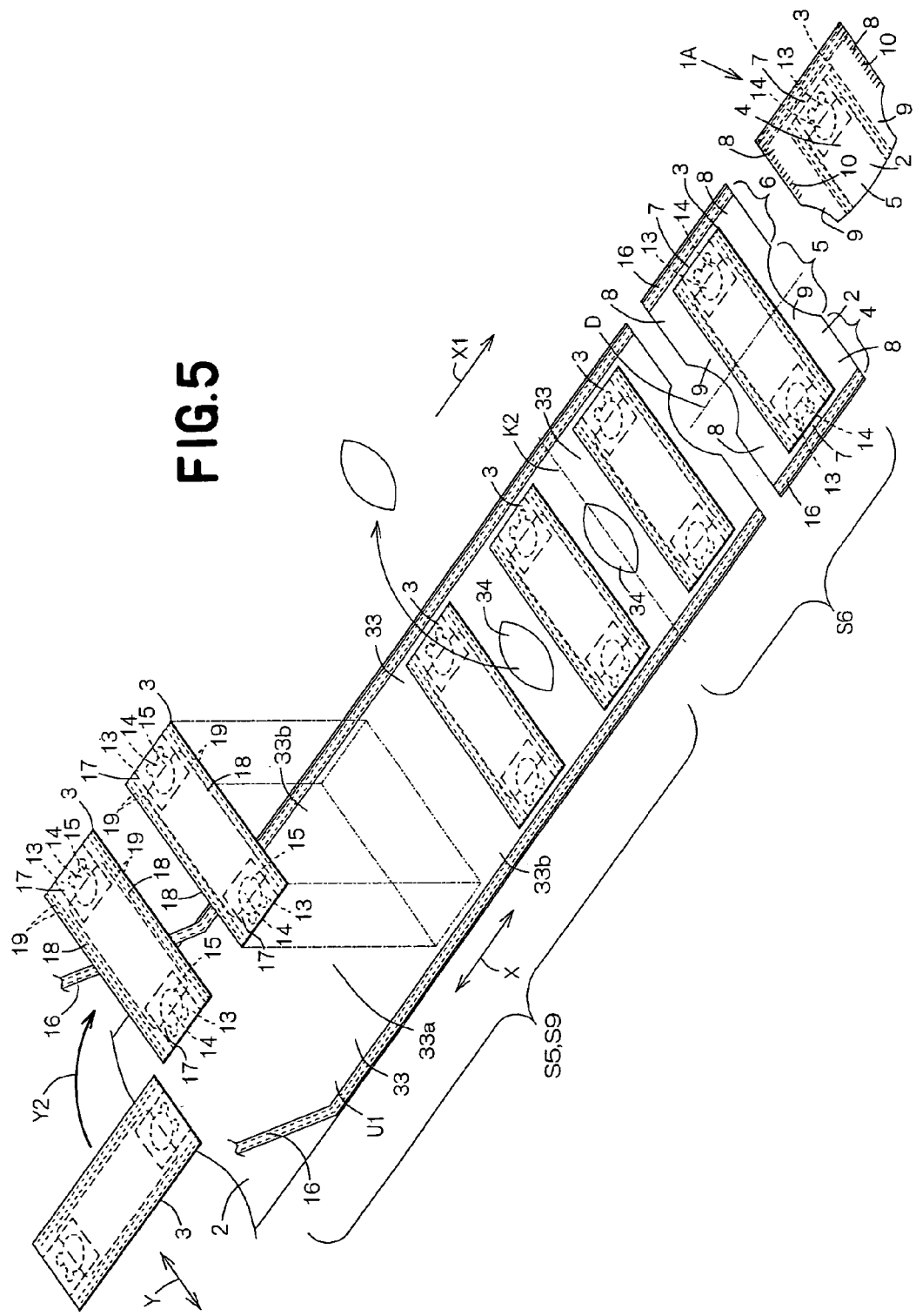
FIG. 5 is a perspective view schematically illustrating steps subsequent to the steps in the process illustrated in FIG. 4.

FIG. 3 is a perspective view schematically illustrating an embodiment of the process for attaching the indicator element, FIG. 4 is a perspective view schematically illustrating the steps subsequent to the steps in the process illustrated in FIG. 3 and FIG. 5 is a perspective view schematically illustrating the steps subsequent to the steps in the process illustrated in FIG. 4. Referring to these Figures, a machine direction is indicated by an arrow X and a cross direction is indicated by an arrow Y. According to this process, the article 1A of FIG. 1 is manufactured and the indicator element 14 is attached in the front and rear waist regions 4, 6 of the article 1A through the successive steps as will be described.

Step of feeding members S1: In the step S1 of feeding members, a plurality of indication sheets 13 each extending in the machine direction are fed at regular intervals onto an outer surface of a continuous first outer layer web 30 while a plurality of the liquid-absorbent cores C each extending in the machine direction are fed at regular intervals onto an inner surface of the first outer layer web 30.

The first outer layer web 30 continuously extends in the machine direction and is running forward at a constant speed in the machine direction. The first outer layer web 30 is formed by the moisture-permeable but hydrophobic fibrous nonwoven fabric layer U2. The indication sheet 13 is formed by the moisture-permeable but liquid-impervious plastic film F1.

The indication sheet 13 is in form of a rectangle, of which the long sides extend in the machine direction, and has a front half 13a and a rear half 13b. The indication sheet 13 is provided in the front and rear halves 13a, 13b with a pair of the indicator elements 14. The indicator elements 14 comprise illustrations 15 of bears' faces printed on an outer surface of the indication sheet 13. These illustrations 15 are in mirror image relationship with each other as viewed in the machine direction. The core C has an hourglass-like planar shape and has a front end zone C1, a rear end zone C3 and an intermediate zone C2 extending between these end zones C1, C3. Transverse dimensions of the indication sheet 13 and the core C are smaller than that of the first outer layer web 30.

Step of placing members S2: In the step of placing members S2, the intermediate zone C2 of the core C is placed between each pair of the indication sheets 13 adjacent to each other in the machine direction; the rear half 13b of the indication sheet A13, that is, the front one of these adjacent indication sheets 13 as viewed in the machine direction, is placed upon the front end zone C1 of the core C; and the front half 13a of the indication sheet B13, that is, the rear one of these adjacent indication sheets 13 as viewed in the machine direction, is placed upon the rear end zone C3 of the core C.

These indication sheets 13 are arranged at regular intervals in the machine direction in a transversely middle zone 30a of the first outer layer web 30 on its outer surface. The cores C are arranged at regular intervals in the machine direction in the transversely middle zone 30a of the first outer layer web 30 on its inner surface. The illustration 15 printed on the rear half 13b of the indication sheet 13 lies in the front end zone C1 of the core C and the illustration 15 printed on the front half 13a of the indication sheet 13 lies in the rear end zones C3 of the core C.

Step of joining members S3: In the step of joining members S3, the indication sheet 13 is joined to the outer surface of the first outer layer web 30 by means of a hot melt adhesive (not shown) and the lower surface of the core C is joined to the inner surface of the first outer layer web 30 by means of a hot melt adhesive (not shown).

Then, a plurality of continuous first stretchable elastic members 19 (leg elastic members) are attached in a stretched state to the inner surface of the outer layer web 30 (step of attaching leg elastic members S7). These elastic members 19 lie on both sides of the core C and extend in the machine direction along transversely opposite side edges 30b of the outer layer web 30 so as to describe substantially straight lines.

After these members have been joined, an inner surface of a continuous inner layer web 31 is placed upon the inner surface of the first outer layer web 30 and an inner surface of a continuous second outer layer web 32 is placed upon the outer surface of the first outer layer web 30. The first outer layer web 30 and the inner layer web 31 have respective inner surfaces joined together by means of a hot melt adhesive (not shown). Thereupon, the upper surface of the core C and the first stretchable elastic members 19 are attached to the inner surface of the inner layer web 31. The inner surface of the first outer layer web 30 and the outer surface of the second outer layer web 32 are joined together by means of a hot melt adhesive (not shown) (step of joining of the second outer layer web S8). The indication sheet 13 and the second outer layer web 32 are left free from each other.

The inner layer web 31 and the second outer layer web 32 travel forward at the same speed as the first outer layer web 30 in the machine direction as indicated by an the arrow X1. The inner layer web 31 is formed by a moisture-permeable but hydrophobic fibrous nonwoven fabric layer U3. The second outer layer web 32 is formed by a moisture-permeable but liquid-impervious plastic film F2. The adhesive is applied on the entire inner and outer surfaces of the first outer layer web 30 and on the entire inner surface of the inner layer web 31 in spiral-, zigzag-, dot- or stripe-pattern.

In the step of joining members S3, it is possible to join the first stretchable elastic members 19 in a stretched state to one of the outer surface of the first outer layer web 30, the inner surface of the inner layer web 31 and the inner surface of the second outer layer web 32. It is possible to eliminate the second outer layer web 32 from the step of joining members S3.

It is also possible to attach the elastic members 19 to the inner surface of the first outer layer web 30 in a stretched state, in any one of the step of feeding members S1 and the step of placing members S2. Furthermore, it is possible to join the second outer layer web 32, in any one of the step of feeding members S1 and the step of placing members S2, to the outer surface of the first outer layer web 30.

Step of forming panels S4: In the step of forming panels S4, the first and second outer layer webs 30, 32, the inner layer web 31 and the indication sheet 13 are cut along each first cutting line K1 to obtain a plurality of the inner panels 3 arranged in the machine direction. The first cutting line K1 extends in the cross direction between each pair of the cores C adjacent to each other in the machine direction. In the step of forming panels S4, the indication sheet 13 is divided into the front half 13a and the rear half 13b. The inner panel 3 has longitudinally opposite end zones 17 extending in the cross direction and transversely opposite side edge zones 18 extending in the machine direction.

Step of joining panels S5: In the step of joining panels S5, the inner panels 3 arranged in the machine direction are successively turned round as indicated by an arrow Y2 approximately by 90°, and then, these inner panels 3 are placed at regular intervals on the inner surface of the continuous outer web 33 destined to be the outer sheet 2. After that, a transversely middle zone 33a is cut away from the portion of the outer web 33 extending between each pair of the inner panels 3 adjacent to each other in the machine direction to form a plurality of openings 34 arranged at regular intervals in the machine direction. Each of these openings 34 has a spindle-shape which is long in the cross direction. Of the inner panel 3 turned round, the longitudinally opposite end zones 17 extend in the machine direction and the transversely opposite side edge zones 18 extend in the transverse direction.

In the step of joining panels S5, the outer surface of the second outer layer web 32 and the inner surface of the outer web 33 are joined to each other by means of a hot melt adhesive (not shown). The adhesive is applied on the entire outer surface of the second outer layer web 32 in spiral-, zigzag-, dot- or striped-pattern.

The outer web 33 continuously extends in the machine direction and runs forward in the machine direction at a constant speed. The outer web 33 is formed by a moisture-permeable but hydrophobic fibrous nonwoven fabric layer U1. Each of the inner panels 3 lie between each pair of the adjacent openings 34 of the outer web 33 so that these inner panels 3 are arranged on the inner surface of the outer web 33 at regular intervals in the machine direction.

In the step of joining panels S5, band-like second stretchable elastic members 16 (waist elastic members) are attached in a stretched state to the inner surface of the outer web 33 (step of attaching waist elastic members S9). The elastic members 16 lie on both sides of the panel 3 and extend in the machine direction along the transversely opposite sides 33b of the outer web 33 so as to describe substantially straight lines. The elastic member 16 comprises band-like fibrous nonwoven fabric layers placed upon each other and a plurality of stretchable elastic members interposed between and secured in a stretched state to these nonwoven fabric layers.

Alternatively, the outer web 33 may be previously formed with a plurality of the openings 34 arranged at regular intervals in the machine direction. In this case, the inner panel 3 will lie on the inner surface of the outer web 33 between each pair of the adjacent openings 34. The openings 34 can be formed by cutting away the transversely middle zones 33a from the outer web 33.

Step of forming articles S6: In the step of forming articles S6, the outer web 33 is cut along each second cutting line K2 so as to obtain a plurality of the articles 1A arranged in the machine direction. The second cutting line K2 lies between each pair of the inner panels adjacent to each other 3 and extends in the cross direction so as to divide the opening 34 in half. The article 1A has a generally hourglass-like planar shape and has the front waist region 4, the rear waist region 6 and the crotch region 5 extending between these waist regions 4, 6.

The article 1A may be folded along a fold guiding line D extending in the machine direction and bisecting a transverse dimension of the outer web 33 as viewed in the cross direction with the inner panel 3 inside and the waist's lateral zones 8 of the front and rear waist regions 4, 6 overlaid may be joined together by means of the heat-sealing lines 10 to form the article 1A in pants-type.

Figure 6:
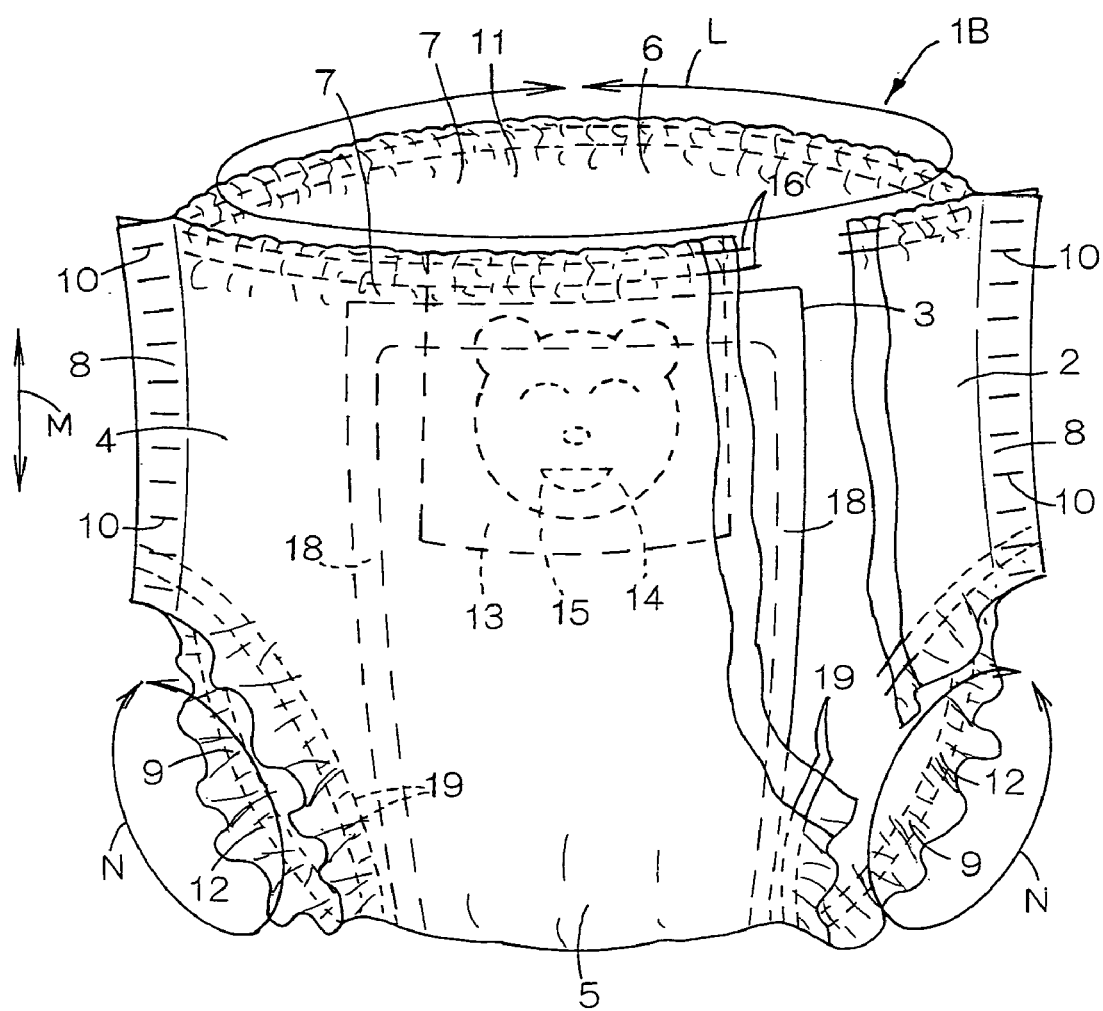
FIG. 6 is a partially cutaway perspective view showing another embodiment of the wearing article according to the invention.
Figure 7:
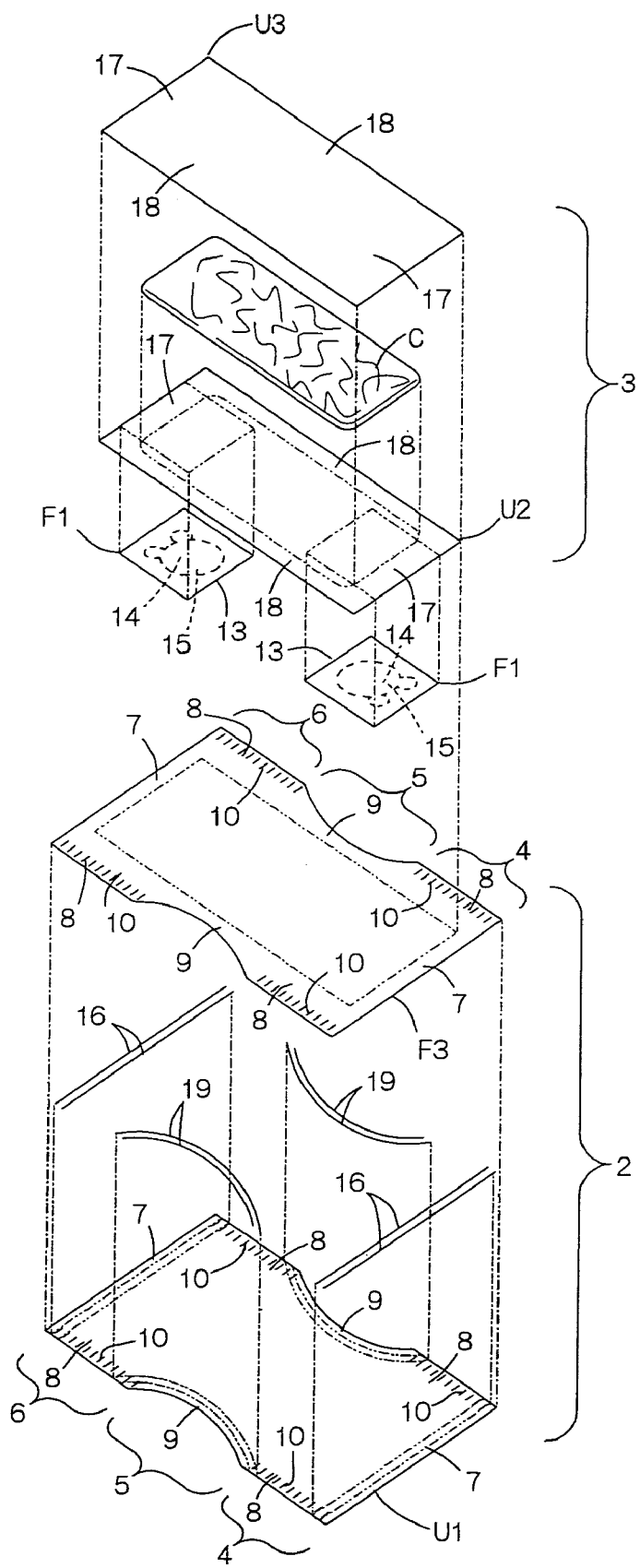
FIG. 7 is an exploded perspective view showing the article shown in FIG. 6.

FIG. 6 is a partially cut away perspective view showing the wearing article 1B according to another embodiment obtained by the method for attaching indicator elements as will be described below and FIG. 7 is an exploded perspective view showing the article 1B showing in FIG. 6. In FIGS. 6 and 7, a waist-surrounding direction is indicated by an arrow L, a longitudinal direction is indicated by an arrow M and a leg-surrounding direction is indicated by an arrow N (in FIG. 6 alone). Expression "inner surfaces" of a fibrous nonwoven fabric layer U1 and a plastic film F3 forming together an outer sheet 2, fibrous nonwoven fabric layers U2, U3 (first outer layer web and inner layer web) forming together an inner panel 3, and an indication sheet 13 refers to surfaces thereof facing a liquid-absorbent core C and expression "outer surfaces" thereof refers to surfaces facing away from the core C.

The article 1B is of pants-type similar to the article 1A shown in FIG. 1 and disposable after used. The article 1B comprises the substantially liquid-impervious outer sheet 2 and the liquid-absorbent inner panel 3 attached to the inner side of the outer sheet 2. The article 1B is composed of front and rear waist regions 4, 6, a crotch region 5 extending between these waist regions 4, 6, a waist-surrounding upper end zone 7, transversely opposite waist's lateral zones 8 and transversely opposite legs' lateral zones 9. The waist's lateral zones 8 are overlaid and joined together by means of a plurality of heat-sealing lines 10 arranged intermittently in the longitudinal direction. The article 1B has a waist-hole 11 and a pair of leg-holes 12 below the waist-hole 11.

The front and rear waist regions 4, 6 are provided in respective transversely middle zones thereof with an indication sheet 13 having indicator elements 14 adapted to be visually recognized from an exterior of the article 1B. Each of the indicator elements 14 comprises an illustration of a bear's face printed on the indication sheet 13.

The outer sheet 2 is formed by the moisture-permeable but hydrophobic fibrous nonwoven fabric layer U1 and the moisture-permeable liquid-impervious plastic film F3 laminated on each other. The nonwoven fabric layer U1 and the film F3 are joined together by means of a hot melt adhesive (not shown). The indication sheet 13 is formed by a moisture-permeable liquid-impervious plastic film F1.

The waist-surrounding upper end zone 7 is provided with band-like waist elastic member 16 (second stretchable elastic member) attached thereto so as to be contractible. The legs' lateral zones 9 are provided with leg elastic members 19 attached thereto in a stretched state. These elastic members 16, 19 are interposed between the nonwoven fabric layer U1 and the film F3 forming together the outer sheet 2 and secured to the surfaces thereof opposed to each other.

The panel 3 extends over the crotch region 5 into the front and rear waist regions 4, 6. The panel 3 is formed by the moisture-permeable but hydrophobic fibrous nonwoven fabric layer U2 (first outer layer web) lying on a side facing away from the wearer's body, the moisture-permeable but hydrophilic fibrous nonwoven fabric layer U3 (inner layer web) lying on a side facing the wearer's body and a liquid-absorbent core C interposed between these nonwoven fabric layers U2, U3 (See FIG. 7).

The panel 3 has longitudinally opposite end zones 17 extending in the waist-surrounding direction and transversely opposite side edge zones 18 extending in the longitudinal direction. Portions of the nonwoven fabric layers U2, U3 extending outward beyond a periphery of the core C have respective inner surfaces overlaid and joined together. The panel 3 is attached to the inner surface of the outer sheet 2 by securing an outer surface of the nonwoven fabric layer U2 to the inner surface of the film F3 by means of a hot melt adhesive (not shown).

These nonwoven fabric layers U2, U3 respectively have their areas slightly larger than those of the upper and lower surfaces of the core C and cover the entire upper and lower surfaces of the core C. The nonwoven fabric layers U2, U3 respectively have their inner surfaces secured to the upper and lower surfaces of the core C by means of a hot melt adhesive (not shown). The indication sheet 13 has its inner surface secured to the outer surface of the nonwoven fabric layer U2 by means of a hot melt adhesive (not shown).

The adhesive is applied on the entire inner and outer surfaces of the nonwoven fabric layer U2, the entire inner surface of the nonwoven fabric layer U3 and the entire outer surface of the film F3. The pattern in which the adhesive is applied on the nonwoven fabric layers U2, U3 and the film F3 is preferably selected from the group consisting of spiral-, zigzag-, dot- and stripe-patterns.

Figure 8:
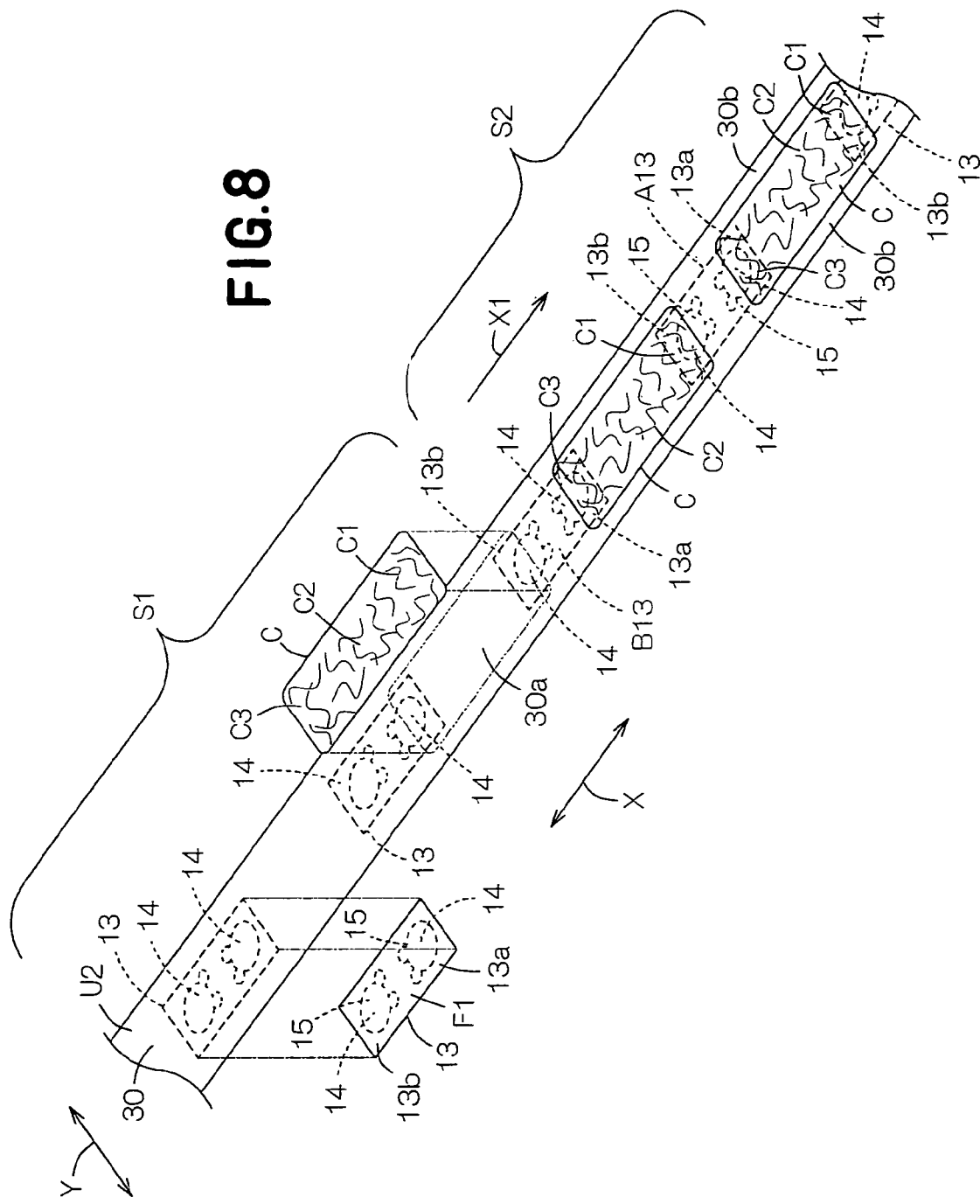
FIG. 8 is a perspective view schematically illustrating another embodiment of the process for attaching an indicator element.

FIG. 8 is a perspective view schematically illustrating another embodiment of the process for attaching the indicator element, FIG. 9 is a perspective view schematically illustrating the steps subsequent to the steps in the process illustrated in FIG. 8 and FIG. 10 is a perspective view schematically illustrating the steps subsequent to the steps in the process illustrated in FIG. 9. Referring to these Figures, a machine direction is indicated by an arrow X and a cross direction is indicated by an arrow Y. According to this process, the article 1B of FIG. 6 is manufactured and the indicator elements 13 are attached in the front and rear waist regions 4, 6 of the article 1B through successive steps as will be described.

Step of feeding members S1: In the step of feeding members S1, a plurality of indication sheets 13 each extending in the machine direction are fed at regular intervals onto an outer surface of a continuous first outer layer web 30 while a plurality of the liquid-absorbent cores C each extending in the machine direction are fed at regular intervals onto an inner surface of the outer layer web 30.

The outer layer web 30 is formed by the moisture-permeable but hydrophobic fibrous nonwoven fabric layer U2. The indication sheet 13 is formed by the moisture-permeable but liquid-impervious plastic film F1. Each of the indication sheets 13 has a front half 13a and a rear half 13b in which the indication sheet 13 is provided with a pair of the indicator elements 14. The indicator elements 14 comprise illustration of bear's faces printed on the outer surface of the indication sheet 13. These illustrations are in mirror image relationship with each other in the machine direction. The core C has, as viewed in the machine direction, a front end zone C1, a rear end zone C3 and an intermediate zone C2 extending between these end zones C1, C3.

Step of placing members S2: In the step of placing members S2, the intermediate zone C2 of the core C is placed between each pair of the indication sheets 13 adjacent to each other in the machine direction; the rear half 13b of the indication sheet A13, that is, the front one of these adjacent indication sheets 13 as viewed in the machine direction, is placed upon the front end zone C1 of the core C; and the front half 13a of the indication sheet B13, that is, the rear one of these adjacent indication sheets 13 as viewed in the machine direction, is placed upon the rear end zone C3 of the core C.

The indication sheets 13 are arranged at regular intervals in the machine direction in a transversely middle zone 30a on its outer surface. The cores C are arranged at regular intervals in the machine direction in the transversely middle zone 30a of the outer layer web 30 on its inner surface. The illustration 15 printed on the rear half 13b of the indication sheet 13 lies in the front end zone C1 of the core C and the illustration 15 printed on the front half 13a of the indication sheet 13 lies in the rear end zone C3 of the core C.

Step of joining members S3: In the step of joining members S3, the indication sheet 13 is joined to the outer surface of the outer layer web 30 by means of a hot melt adhesive (not shown) and the lower surface of the core C is joined to the inner surface of the outer layer web 30 by means of a hot melt adhesive (not shown). After there members have been joined, the inner surface of the outer layer web 30 is placed upon an inner surface of the continuous inner layer web 31 and the inner surfaces of these webs 30, 31 are joined together by means of a hot melt adhesive (not shown). At the same time, the upper surface of the core C is attached to the inner surface of the inner layer web 31.

The inner layer web 31 is formed by the moisture-permeable and hydrophilic fibrous nonwoven fabric layer U3. The adhesive is applied on the entire inner and outer surfaces of the outer layer web 30 and the entire inner surface of the inner layer web 31 in spiral-, zigzag-, dot- or stripe-pattern.

Step of S4: In the step of forming panels S4, the outer layer web 30, the inner layer web 31 and the indication sheet 13 are cut along each first cutting line K1 to obtain a plurality of the inner panels 3 arranged in the machine direction. The first cutting line K1 extends in the cross direction between each pair of the cores C adjacent to each other in the machine direction. In the step of forming panels step S4, the indication sheet 13 is divided into the front half 13a and the rear half 13b. The inner panel 3 has longitudinally opposite end zones 17 extending in the cross direction and transversely opposite side edge zones 18 extending in the machine direction.

Step of joining panels S5: In the step of joining panels S5, after the inner panels 3 arranged in the machine direction are successively turned round as indicated by an arrow Y2 approximately by 90°, and then, these inner panels 3 are placed at regular intervals on the inner surface of the continuous outer web 33. In the step of joining panels S5, the outer surface of the outer layer web 30 and the inner surface of the outer web 33 are joined together by means of a hot melt adhesive (not shown).

The outer web 33 is formed by the moisture-permeable but hydrophobic fibrous nonwoven fabric layer U1 and the moisture-permeable but liquid-impervious plastic film F3 laminated on each other. The outer web 33 has a plurality of openings 34 arranged in the machine direction at regular intervals. The nonwoven fabric layer U1 and the film F3 opposed to each other are joined together by means of a hot melt adhesive (not shown). Each of these openings 34 has a spindle-shape which is relatively long in the cross direction and the opening 34 is formed by cutting a corresponding portion away from the transversely middle zones 33a of the outer web 33.

A plurality of stretchable elastic members 19 (leg elastic members) are attached in a stretched state to the periphery of the opening 34. These elastic members 19 are interposed between the nonwoven fabric layer U1 and the film F3 and attached to the surfaces thereof opposed to each other. The inner panel 3 is located between each pair of the adjacent openings 34 of the outer web 33 so that the inner panels 3 are arranged on the inner surface of the outer web 33 at regular intervals in the machine direction.

In the step of joining panels S5, a plurality of second stretchable elastic members 16 (waist elastic members) are attached in a stretched state to the outer web 33 by means of a hot melt adhesive (not shown) (step of attaching waist elastic members S9). These elastic members 16 lie on both sides of the panel 3 and extend in the machine direction along transversely opposite side edges 33b of the outer web 33 so as to describe substantially straight lines. These elastic members 16 are interposed between the nonwoven fabric layer U1 and the film F3 and attached to the surfaces thereof opposed to each other.

Step of forming articles S6: In the step of forming articles S6, the outer web 33 is cut along each second cutting line K2 to obtain a plurality of the articles 1B arranged in the machine direction. The second cutting line K2 extends in the cross direction between each pair of the adjacent inner panels 3. The article 1B has, in the cross direction, a front waist region 4, a rear waist region 6 and a crotch region 5 extending between these two waist regions 4, 6.

The article 1B may be folded along a fold guiding line D extending in the machine direction and bisecting a dimension of the outer web 33 as viewed in the cross direction with the inner panel 3 inside and the waist's lateral zones 8 of the front and rear waist regions 4, 6 overlaid may be joined together by means of the heat-sealing lines 10 to form the article 1B in pants-type.

It is possible to form the first outer layer web 30 by a moisture-permeable but liquid-impervious plastic film. It is possible to form the second outer layer web 32 by a moisture-permeable but hydrophobic fibrous nonwoven fabric layer. It is also possible to form the outer web 33 by a composite nonwoven fabric layer comprising two layers of moisture-permeable but hydrophobic fibrous nonwoven fabric laminated with each other.

A stock material for the fibrous nonwoven fabric layers U1, U2, U3 may be selected from the group consisting of those obtained by spun lace-, needle punch-, melt blown-, thermal bond-, spun bond-, chemical bond- and air through-processes. The component fibers of the nonwoven fabric layers U1, U2, U3 may be selected from the group consisting of polyolefin-, polyester- and polyamide-based fibers and core-and-sheath or side-by-side conjugated fibers of polyethylene/polypropylene or polyethylene/polyester. The plastic films F1, F2, F3 are preferably made of polyolefin-based thermoplastic synthetic resin.

The present invention is applicable to, in addition to the pull-on disposable articles 1A, 1B having its front and rear waist regions 4, 6 previously connected with each other, also to an open-type disposable wearing article having its front and rear waist regions connected with each other immediately before put on the wearer's body. In the case of the open-type disposable wearing article, the step of forming articles includes no step of folding the article and, instead of this, a target tape strip may be attached to the outer surface of the outer web in the front waist region of the article and a pair of tape fasteners adapted to be anchored on the target tape strip may be attached to the waist's lateral zones in the rear waist region, respectively.

The process according to this invention for attaching the indicator element is primarily characterized in that the indication sheet having a pair of indicator elements on the front and rear halves, respectively, is divided in two so that the indicator elements can be attached to each of the front and rear regions of the article all at once in the course of manufacturing a plurality of the articles arranged in the machine direction. This process makes it unnecessary to use means as well as steps for separately attaching the individual indicator elements to the front and rear waist regions. In this way, the indicator elements can be continuously attached to the front and rear regions of the articles at a high speed, on one hand, and the manufacturing cost can be reduced, on the other hand.

According to this process, the indication sheet having a pair of the illustrations printed on the indication sheet are in the mirror image relationship with each other in the machine direction and therefore there is no possibility that one of these illustrations respectively formed on the front and rear regions might be placed upside down with respect to the other illustration.

What is claimed is:

1. A process of attaching, in front and rear regions of a disposable garment which comprises an outer sheet and a liquid-absorbent inner panel attached to said outer sheet, indicator elements which are visually recognizable from an exterior of said garment, said process comprising the steps of:

feeding a plurality of liquid-absorbent cores each having front and rear end zones and an intermediate zone and running in a machine direction onto an inner surface of one of a continuous first outer layer web and a continuous inner layer web running in the machine direction and destined to be said outer sheet, while feeding a plurality of indication sheets each extending in said machine direction and having said indicator elements in front and rear halves thereof, respectively, at regular intervals in said machine direction onto an outer surface of said first outer layer web;

placing said intermediate zone of each said core between each pair of said indication sheets adjacent to each other in said machine direction so that the rear half of a front one of said indication sheets adjacent to each other in said machine direction is placed upon said front end zone of said core, and the front half of a rear one of said indication sheets adjacent to each other in said machine direction is placed upon said rear end zone of said core;

joining each said indication sheet to said first outer layer web, joining each said core to at least one of said inner layer web and said first outer layer web, and joining inner surfaces of said inner layer web and said first outer layer web which are overlaid on each other;

cutting said indication sheets together with said inner and first outer layer webs in a cross direction between each pair of said cores adjacent to each other in said machine direction, so that each said indication sheet is divided into said front and rear halves, to obtain a plurality of said inner panels arranged in said machine direction; and placing said inner panels at regular intervals on an inner surface of a continuous outer web running in said machine direction after said inner panels are turned approximately by 90° to the cross direction, and joining said outer surface of said first outer layer web to the inner surface of said outer web.

2. The process according to claim 1, further includes the steps of cutting said outer web in a transversely middle zone to form a plurality of openings arranged at regular intervals in said machine direction, then, placing, between each pair of said openings adjacent to each other of said outer web, one of said inner panels that has been turned approximately by 90° to the cross direction; and cutting said outer web in said cross direction between each pair of said inner panels adjacent to each other to form a plurality of said garments arranged in said machine direction.

3. The process according to claim 1, further comprising the steps of turning said inner panels approximately by 90° to the cross direction while placing said inner panels on said inner surface of said outer web at regular intervals in said machine direction and, then, cutting a transversely middle zone of said outer web extending between each pair of said inner panels adjacent to each other to form a plurality of openings arranged at regular intervals in said machine direction; and cutting said outer web in said cross direction between each pair of said inner panels adjacent to each other to form a plurality of said garments arranged in said machine direction.

4. The process according to claim 1, further comprising the steps of placing an inner surface of a continuous second outer layer web running in said machine direction upon said outer surface of said first outer layer web, and joining said first outer layer web to said second outer layer web;

cutting said indication sheets together with said first and second outer layer webs and said inner layer web in said cross direction between each pair of said cores adjacent to each other in said machine direction; and joining an outer surface of said second outer layer web to said inner surface of said outer web.

5. The process according to claim 1, further comprising the step of attaching first stretchable elastic members lying on both sides of said cores and extending in said machine direction in a stretched state to one of the inner surface of said first outer layer web and the inner surface of said inner layer web.

6. The process to claim 4, further comprising the step of attaching first stretchable elastic members lying on both sides of said cores and extending in said machine direction in a stretched state to one of said outer surface of said first outer layer web and said inner surface of said second outer layer web.

7. The process according to claim 1, further comprising the step of attaching second stretchable elastic members lying on both sides of said outer web and extending in said machine direction in a stretched state to said outer web.

8. The process according to claim 4, wherein said first and second outer layer webs are formed by one of (i) a moisture-permeable hydrophobic fibrous nonwoven fabric and (ii) a moisture-permeable liquid-impervious plastic film, and said inner layer web is formed by a hydrophilic fibrous nonwoven fabric.

9. The process according to claim 1, wherein said outer layer web is formed by one of (i) a moisture-permeable hydrophobic fibrous nonwoven fabric, (ii) a composite nonwoven fabric consisting of moisture-permeable but hydrophobic fibrous nonwoven fabric layers laminated one with another, and (iii) a composite sheet consisting of a moisture-permeable but hydrophobic fibrous nonwoven fabric and a moisture-permeable but liquid-impervious plastic film laminated with each other.

10. The process according to claim 1, wherein each said indication sheet is formed by one of (i) a moisture-permeable but hydrophobic fibrous nonwoven fabric and (ii) a moisture-permeable but liquid-impervious plastic film.

11. The process according to claim 1, wherein said indicator elements comprise a pair of illustrations respectively printed on said front and rear halves of each said indication sheet and adjacent to each other in said machine direction.

* * * * *